United States Patent [19]

Tezuka

[11] Patent Number: 4,810,341
[45] Date of Patent: Mar. 7, 1989

[54] METHOD OF MAKING ELECTROPHORESIS SHEET

[75] Inventor: Sigeru Tezuka, Saitama, Japan

[73] Assignee: Fuji Photo Film Co., Ltd., Kanagawa, Japan

[21] Appl. No.: 27,660

[22] Filed: Mar. 19, 1987

[30] Foreign Application Priority Data

Mar. 20, 1986 [JP] Japan .................................. 61-63373

[51] Int. Cl.$^4$ ............................................. G01N 27/28
[52] U.S. Cl. ............................... 204/182.8; 204/299 R; 204/180.1
[58] Field of Search ............. 204/182.8, 299 R, 180.1; 83/861; 156/256, 243

[56] References Cited

U.S. PATENT DOCUMENTS

| 3,635,808 | 1/1972 | Elevitch | 204/299 R |
| 3,767,560 | 10/1973 | Elevitch | 204/299 R |
| 4,699,680 | 11/1987 | Shiraishi et al. | 204/180.1 X |

Primary Examiner—John F. Niebling
Assistant Examiner—John S. Starsiak, Jr.
Attorney, Agent, or Firm—Jules E. Goldberg

[57] ABSTRACT

A method of making an electrophoresis sheet composed of two sheet members formed of a non-conductive organic polymer film and disposed to stand facing each other, spacers having predetermined thicknesses disposed at both edge portions between the two sheet members, and an electrophoresis gel membrane of uniform thickness provided with slots extending from an upper edge portion towards a center and grasped between the two sheet members, comprises the step of forming the slots by pushing a cutting blade member against a gel membrane web before the gel membrane web is grasped between the sheet members. The cutting blade member is composed of a combination of a single linear transverse blade having a plurality of cutaway portions and disposed to extend in a transverse direction of the gel membrane web, with a plurality of linear longitudinal blades continuing to the linear transverse blade at both ends of each of the cutaway portions.

5 Claims, 4 Drawing Sheets

METHOD OF MAKING ELECTROPHORESIS SHEET

BACKGROUND OF THE INVENTION

1. Field of the Invention

This invention relates to a method of making an electrophoresis sheet used for separation, analysis or the like of a substance having an electrically dissociated group in a solution, like protein or nucleic acid, on the basis of a difference in the electric charge and molecular weight of the particles.

2. Description of the Prior Art

There has heretofore been known an operation of electrophoresis by which separation of a substance by utilizing migration of charged molecules or particles of protein, nucleic acid, their decomposition products, or the like, is effected in a sheet-like medium such as a gel membrane or a filter paper impregnated with a buffer solution under the effect of an electric field. The electrophoresis is utilized particularly for separation and fixation of the high molecular weight substances of the living body as mentioned above.

Particularly, in the generic engineering which has attracted attention in recent years, the electrophoresis operation is indispensable for determining a base sequence in the molecule of nucleic acid such as DNA by utilizing autoradiography. In general, the electrophoresis operation for this purpose includes the step of subjecting a series of mixtures of base-specific reaction products of DNA or DNA fragments provided with a radioactive label to migration in the electric field inside of an electrophoresis medium, whereby the mixtures migrate in parallel with each other in the direction of the electric field. The migration pattern of multiple rows obtained after the migration (a group of zones formed by electrophoresis on the medium) is recorded as an autoradiograph, and then the base arrangement is determined by comparing positions of the zones in the respective rows with each other. The comparison is carried out based on the electrophoresis principle that base-specific reaction products having equal molecular weights migrate by equal distances if the electrophoresis is started from the same line.

In general, filter paper, a membrane filter, a starch gel membrane, a polyacrylamide gel membrane or the like is used as the electrophoresis medium in the form of a sheet having a uniform thickness. In the case where a gel membrane such as a starch gel membrane or a polyacrylamide gel membrane is used, the liquid for gel preparation has heretofore been introduced into a mold constituted by disposing a supporting frame (spacer) around a flat supporting member formed of a non-conductive material such as a glass plate, and gelled for use as the gel membrane, after the upper surface is enclosed by a different supporting member if necessary. However, this method of forming a gel membrane is very troublesome as it requires complicated operations prior to the electrophoresis operation.

Accordingly, as disclosed in, for example, Japanese Unexamined Patent Publication No. 59(1984)-126237, the applicant proposed an electrophoresis sheet which requires no troublesome operations of gel preparation and is easy to use. The proposed electrophoresis sheet comprises two sheet members formed of a non-conductive organic polymer film and disposed to stand facing each other, spacers having predetermined thicknesses disposed at both edge portions between the two sheet members, and an electrophoresis gel membrane enclosed between the two sheet members in a uniform thickness. With the proposed electrophoresis sheet, since the gel membrane can be supplied in the form disposed between the two polymer films, the operators can purchase the electrophoresis sheets and easily carry out the electrophoresis operation.

The aforesaid electrophoresis sheet is provided with slots for introducing and holding the substance subjected to the electrophoresis at an upper edge portion of the gel membrane as the electrophoresis medium, i.e. at the edge portion which does not stand facing the aforesaid spacers and is positioned on the upper side in the course of the electrophoresis operation. The slots extend from the upper edge portion of the gel membrane toward the center thereof and are ordinarily formed side by side in the transverse direction of the gel membrane. In the case where the gel membrane is formed by pouring the liquid for gel preparation into the space between the flat plate-like supporting members formed of glass plates or the like as mentioned above, a comb-like member generally called a sample comb is disposed between the supporting members before the liquid for gel preparation is poured, and removed after gelling of the liquid, thereby to form the slots. However, in the course of making the aforesaid electrophoresis sheet, since pouring of the liquid for gel preparation is not carried out, but instead a gel membrane web already gelled is supported between the sheet members, the slots are formed by punching or cutting of the gel membrane web. Cutting of the slots has heretofore been carried out by, for example, pushing a cutting blade 70 having a shape as shown in FIG. 9 gainst a gel membrane web 71W. The conventional cutting blade 70 is formed into the slot shape by, for example, electrical discharge machining. However, the cutting edge portion of the cutting blade 70 made in this manner is not sharp, but instead substantially has a thickness. Therefore, as shown in FIG. 10, a gel membrane 71 having slots 72, 72, . . . cut by use of the cutting blade 70 becomes such that a corner 72a of each of the slots 72, 72, . . . is round and a closed edge portion 72b has a collapsed rough surface instead of a sharp cut surface. As a result, a substance 73 introduced and held in the slots 72, 72, . . . for electrophoresis becomes a dumpling-like form, and the obtained migration pattern is distorted and cannot be discriminated, or the migration pattern reading accuracy becomes low. Low accuracy of the migration pattern reading results in low reliability of the obtained information on the base sequence in nucleic acid or the like.

SUMMARY OF THE INVENTION

The primary object of the present invention is to provide a method of making an electrophoresis sheet wherein cut surfaces and corners of slots are formed to be substantially sharp.

Another object of the present invention is to provide a method of making an electrophoresis sheet which improves reliability of the information obtained by electrophoresis.

The present invention provides a method of making an electrophoresis sheet composed of two sheet members formed of a non-conductive organic polymer film and disposed to stand facing each other, spacers having predetermined thicknesses disposed at both edge portions between the two sheet members, and an electrophoresis gel membrane of uniform thickness provided with slots extending from an upper edge portion towards a center and grasped between the two sheet members, wherein the improvement comprises the step of forming said slots by pushing a cutting blade member against a gel membrane web before said gel membrane web is grasped between said sheet members, said cutting blade member being composed of a combination of a single linear transverse blade having a plurality of cutaway portions and disposed to extend in a transverse direction of said gel membrane web, with a plurality of linear longitudinal blades continuing to said linear transverse blade at both ends of each of said cutaway portions.

With the method of making an electrophoresis sheet in accordance with the present invention, it is possible to obtain an electrophoresis sheet whose gel membrane has slots having corners finished sharply without being rounded, and migration start edge portions finished to be a sharp cut surface and aligning in a line. Accordingly, when the electrophoresis sheet made by the method of the present invention is used, it is possible to obtain a migration pattern free from distortion and started from the migration start positions aligning with each other, to substantially improve the migration pattern reading accuracy, and to improve the accuracy of the information obtained by comparison of multiple migration rows.

DESCRIPTION OF THE PREFERRED EMBODIMENTS

The present invention will hereinbelow be described in further detail with reference to the accompanying drawings.

Figure 1:
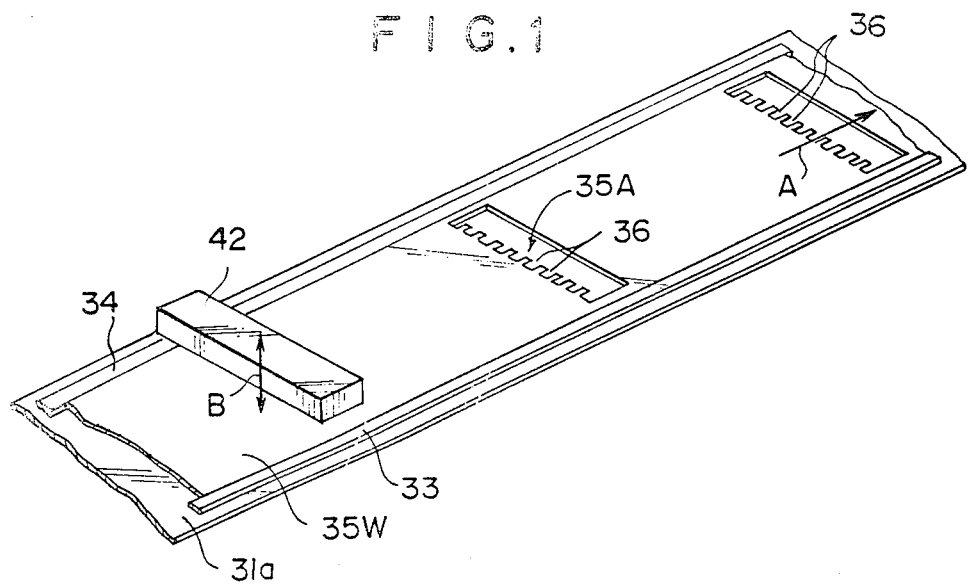
FIGS. 1 and 2 are perspective views showing the steps of making an electrophoresis sheet by an embodiment of the method in accordance with the present invention.

Referring to FIG. 1, elongated spacers 33 and 34 are disposed on both side edge portions of a sheet member (base film) 31a as described later, and a gel membrane web 35W is disposed between the spacers 33 and 34. The sheet member 31a on which the gel membrane web 35W is disposed is conveyed by a known conveyance means (not shown) in the direction as indicated by the arrow A. The gel membrane web 35W may be of any type insofar as electrophoresis can be effected therein and may be, for example, an acryl amide gel membrane, an agarose gel membrane, a starch gel membrane, an agar gel membrane, a cellulose acetate porous membrane, or filter paper. Above the gel membrane web 35W, a cutting blade member 42 is disposed normal to the conveyance direction A of the gel membrane web 35W. The cutting blade member 42 is moveable vertically, i.e. in the direction as indicated by the arrow B, by a known mechanism interlocked with start and stop of the web conveyance means. Specifically, when the web conveyance means is stopped, the cutting blade member 42 is moved down and pushed against the gel membrane web 35W. Then, when the cutting blade member 42 is moved up, the web conveyance means is moved by a predetermined distance and stopped. The cutting blade member 42 is thereafter moved down as mentioned above. The aforesaid operations are repeated subsequently.

The lower surface side of the cutting blade member 42 in FIG. 1 is provided with cutting blades having shapes adapted to desired shapes of slots of a gel membrane as described later. As the aforesaid operations are repeated, openings 35A, 35A, . . . are sequentially formed through the gel membrane web 35W, and a plurality of slots 36, 36, . . . standing side by side in the transverse direction of each of the openings 35A, 35A, . . . , i.e. in the width direction thereof, are formed at one edge portion of each of the openings 35, 35, . . . , i.e. at the edge portion of the gel membrane facing up when the gel membrane is used for electrophoresis.

Figure 2:
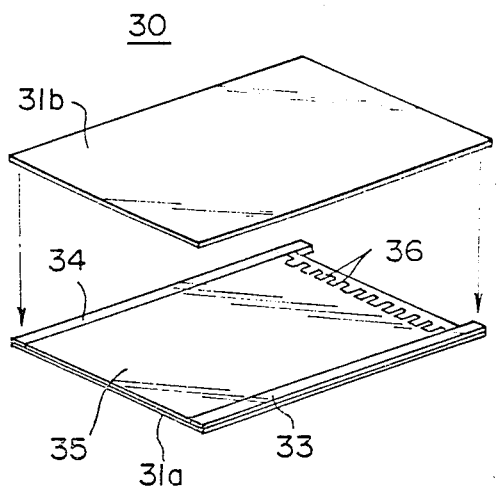

After the openings 35A, 35A, . . . are formed through the gel membrane web 35W as mentioned above, the gel membrane web 35W is cut together with the spacers 33 and 34, the sheet member 31a, and a sheet member web (cover film web) 31b disposed on the gel membrane web 35W, whereby a gel membrane sheet 35 as shown in FIG. 2 is obtained. The gel membrane sheet 35 is in the condition disposed between the spacers 33 and 34 on the sheet member 31a, and the sheet member 31b is overlaid on the gel membrane sheet 35 to constitute an electrophoresis sheet 30. The sheet members 31a and 31b are formed of a non-conductive organic polymer film. As the sheet members 31a and 31b, any material may be used insofar as it has good surface flatness and is non-conductive and substantially impermeable to water. For this purpose, it is possible to use, for example, a polyester such as polyethylene terephthalate or polycarbonate of bisphenol A, polymethyl methacrylate, polyethylene, polystyrene, a vinyl polymer such as polyvinyl chloride, a polyamide such as nylon, or a copolymer of the monomers mentioned above, e.g. vinylidene chloride-vinyl chloride copolymer. The materials of the sheet members 31a and 31b may be identical or different. The sheet member 31b (which is otherwise called the cover sheet) on the upper side in FIG. 2 should preferably be as thin as practicable for enabling exposure for autoradiography therethrough. Thus the thickness of the front sheet member 31b is approximately 50 μm or less, preferably within the range of approximately 3 μm to approximately 50 μm, more preferably within the range of approximately 5 μm to approximately 40 μm. The thickness of the rear sheet member 31a may be equal to or different from the thickness of the front sheet member 31b, and may be within the range of approximately 5 μm to approximately 5 mm, preferably within the range of approximately 8 μm to approximately 3 mm.

Figure 3:
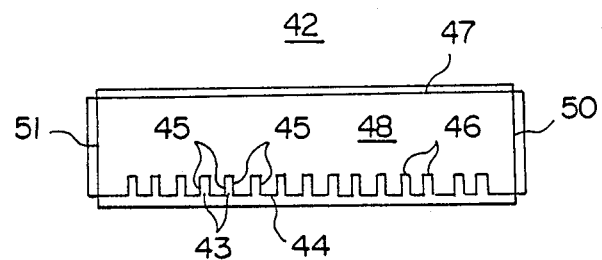
FIGS. 3 and 4 are a plan view and an exploded perspective view showing the cutting blade member used in the embodiment of the method in accordance with the present invention.

The cutting blade member 42 will hereinbelow be described in detail with reference to FIGS. 3 and 4. FIG. 3 shows the cutting blade side of the cutting blade member 42, i.e. the lower surface side thereof in FIG. 1. As shown in FIG. 3, the cutting blade member 42 is provided with a linear transverse blade 44 having cutaway portions 43, 43, . . . at predetermined intervals and extending in the transverse direction, i.e. in the right-left direction in FIG. 3, a plurality of small linear longitudinal blades 45, 45, . . . continuing to the linear transverse blade 44 at both ends of each of the cutaway portions 43, 43, . . . , end blades 46, 46, . . . each of which continues to the two adjacent linear longitudinal blades 45, 45 and stands facing each of the cutaway portions 43, 43, . . . , a rear edge cutting blade 47 extending in parallel with the linear transverse blade 44, and side blades 50 and 51 continuing to the end portions of the rear edge cutting blade 47 and the end portions of the linear transverse blade 44.

Figure 4:
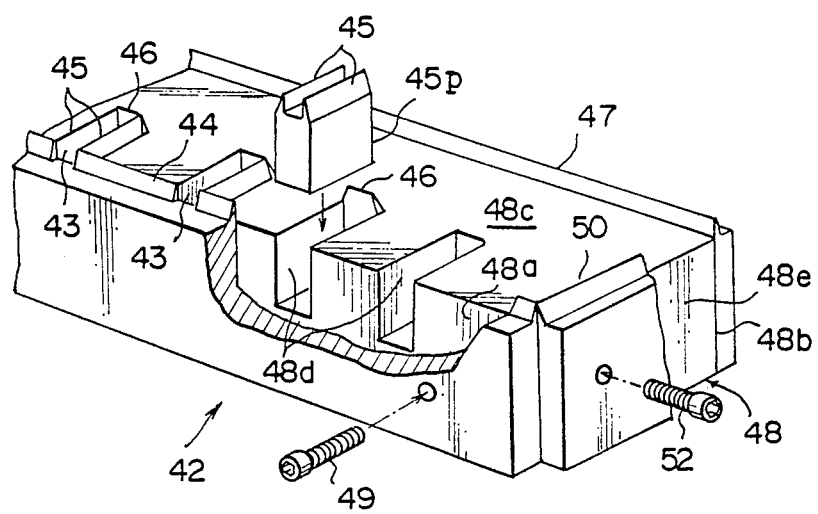

As shown in detail in FIG. 4, the linear transverse blade 44 is constituted by a single member, and secured to a front face 48a of a rectangular prism-like base 48 by use of, for example, a bolt 49. Each of the side blades 50 and 51 is secured to a side face 48e of the base 48 by use of a bolt 52. The rear edge cutting blade 47 is secured to a rear face 48b of the base 48 by use of a bolt (not shown). A plurality of small square holes 48d, 48d, . . . opened to the front face 48a and a lower face 48c (i.e. the upper face in FIG. 4) of the base 48 are formed to stand side by side in the base 48. A longitudinal blade piece 45P and one of the aforesaid end blades 46, 46, . . . are fitted and secured to adjoin each other in each of the square holes 48d, 48d, . . . . The longitudinal blade piece 45P is provided with the linear longitudinal blades 45, 45 extending in parallel with each other and secured in the square hole 48d so that the linear longitudinal blades 45, 45 continue to the linear transverse blade 44 at both ends of the cutaway portion 43 as mentioned above. In this embodiment, the linear transverse blade 44 and the linear longitudinal blades 45, 45, . . . are disposed normal to each other.

Figure 5:
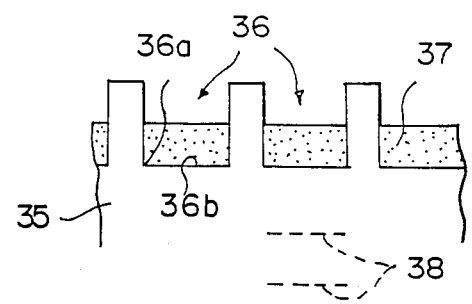
FIG. 5 is an enlarged plan view showing the slot section of the gel membrane of the electrophoresis sheet made by the embodiment of the method in accordance with the present invention.

The cutting blade member 42 constituted as mentioned above is disposed so that the linear transverse blade 44 extends in the width direction of the gel membrane web 35W in FIG. 1. Therefore, as the cutting blade member 42 is moved up and down, and as conveyance and stopping of the gel membrane web 35W are repeated, the slots 36, 36, . . . are cut and formed at one edge portion of the gel membrane opening 35A, i.e. at the edge portion constituting the upper edge portion of the gel membrane sheet 35, by the linear transverse blade 44, the linear longitudinal blades 45, 45, . . . and the end blades 46, 46, . . . . Also, the other edge portion of the opening 35A, i.e. the edge portion constituting the rear edge portion of an individual gel membrane sheet 35 adjacent to the gel membrane sheet 35 whose slots 36, 36, . . . have been formed as mentioned above, is cut by the rear edge cutting blade 47. Both side edges of the opening 35A is cut by the side blades 50 and 51. The gel membrane at the section cut out in this manner is separated from the gel membrane web 35W and discharged. FIG. 5 is an enlarged view showing the region of the slots 36, 36, . . . formed as mentioned above. Since the slots 36, 36, . . . are formed by cutting with the single linear transverse blade 44 and the linear longitudinal blades 45, 45, . . . combined with the linear transverse blade 44, a corner 36a of each of the slots 36, 36, . . . does not become round, but instead has a shape defined by two straight lines intersecting with each other (a right-angled shape in this embodiment) as shown in FIG. 5. Also, the closed edge portion 36b, 36b, . . . of the slots 36, 36, . . ., which act as the electrophoresis start edge portions are constituted by substantially sharp cut surfaces and aligned in a line.

Figure 6:
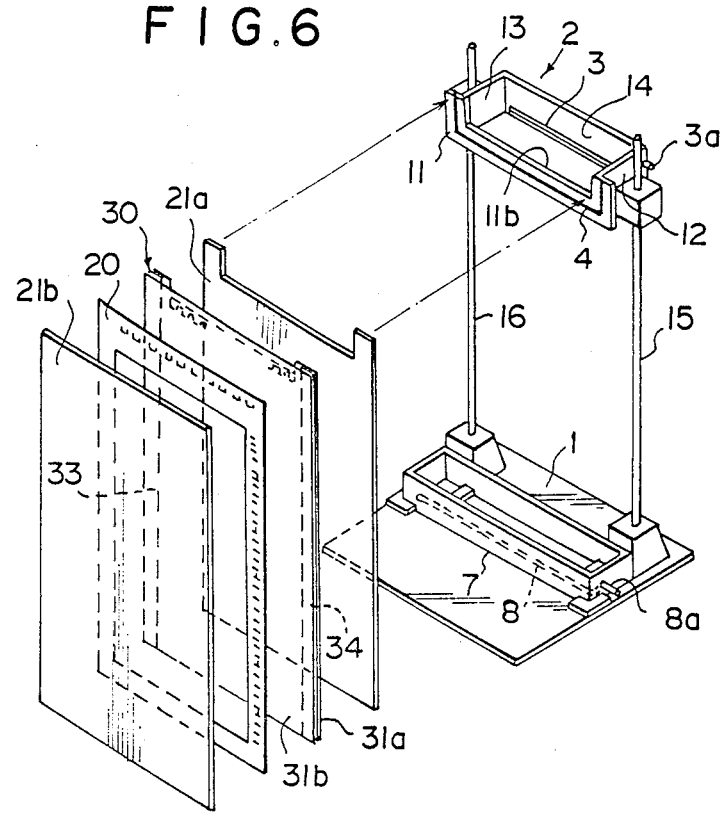
FIG. 6 is a perspective view showing an example of the electrophoresis apparatus wherein the electrophoresis sheet made by the method in accordance with the present invention is used.

The operation of electrophoresis carried out by use of the electrophoresis sheet 30 will hereinbelow be described with reference to FIG. 6. Basically, the electrophoresis apparatus shown in FIG. 6 is composed of a supporting base 1, and an upper buffer solution vessel 2 and a lower buffer solution vessel 7 which are mounted on the supporting base 1. An upper electrode 3 and a lower electrode 8 constituted by a single platinum wire extending in the width direction of the apparatus are respectively disposed in the upper buffer solution vessel 2 and the lower buffer solution vessel 7, so that the electrodes 3 and 8 are dipped in a buffer solution when the buffer solution is introduced into the upper buffer solution vessel 2 and the lower buffer solution vessel 7. The electrodes 3 and 8 are respectively connected to external terminals 3a and 8a projecting outwardly from the side walls of the upper buffer solution vessel 2 and the lower buffer solution vessel 7. The upper buffer solution vessel 2 is defined by side plates 12 and 13, a rear and bottom plate 14, and a front plate 11, and is formed with the upper surface open. A cutaway portion 11b is formed at the upper section of the front plate 11. The side plates 12 and 13 are supported by supporting rods 15 and 16 secured to the supporting base 1, whereby the upper buffer solution vessel 2 secured at the high position above the supporting base 1.

The electrophoresis sheet 30 is grasped between flat plate-like supporting members 21a and 21b formed of glass plates, ceramic plates, or the like, and the flat plate-like supporting members 21a and 21b are secured in this condition to the front side of the front plate 11 by use of, for example, clips. In this condition, a packing is provided on the surface of the front plate 11 so that a buffer solution does not leak between the contact surfaces of the supporting member 21a and the front plate 11. Also, in this example, a square frame-like spacer 20 is disposed between the flat plate-like supporting member 21b farther form the upper buffer solution vessel 2 and the electrophoresis sheet 30. The spacer 20 having this shape contacts only the end portions of the electrophoresis sheet 30 when the electrophoresis sheet 30 is grasped between the flat plate-like supporting members 21a and 21b. Therefore, the center portion of the very thin and flexible sheet member 31b, i.e. the portion thereof facing the gel membrane 35 utilized for electrophoresis, is spaced from the supporting member 21b by a distance equal to the thickness of the spacer 20.

After the flat plate-like supporting members 21a and 21b having the electrophoresis sheet 30 grasped therebetween are secured to the upper buffer solution vessel 2, i.e. to the front frame 11, the buffer solution is introduced into the upper buffer solution vessel 2 and the lower buffer solution vessel 7. A predetermined voltage is then applied across the external terminals 3a and 8a for carrying out electrophoresis. A cutaway portion like a cutaway portion 11b at the upper end of the front plate 11 is formed at the upper end of the supporting member 21a closer to the front plate 11, and the buffer solution in the upper buffer solution vessel 2 contacts the upper end of the gel membrane 35 via the cutaway portion. On the other hand, the lower end of the electrophoresis sheet 30 is projected into the lower buffer solution vessel 7, so that the lower end of the gel membrane 35 contacts the buffer solution in the lower buffer solution vessel 7. Accordingly, the voltage applied across the external terminals 3a and 8a acts on the gel membrane 35 via the buffer solution, and electrophoresis of a substance such as protein or nucleic acid introduced from the upper end of the gel membrane 35 into the slots 36, 36, . . . is carried out.

In the apparatus of FIG. 6, since the spacer 20 is disposed, the center of the thin and flexible sheet member 31b is slightly spaced from the supporting member 21b. Therefore, even though dust or the like is present on the surface of the sheet member 31b or on the surface of the supporting member 21b, there is no risk of the gel membrane 35 being dimpled by dust or the like. Accordingly, no distortion is caused in the migration pattern by dimpling of the gel membrane 35, and the migration pattern can be read accurately.

Also, with the electrophoresis sheet 30 made by the method of the present invention, since the slot corners 36a, 36a, . . . of the gel membrane 35 are at right angles as shown in FIG. 5 instead of being rounded, the substance 37 introduced and held in the slots 36, 36, . . . does not become a dumpling form. Therefore, as shown in FIG. 5, a migration pattern 38 becomes a straight line form without being distorted, and the reading accuracy of the migration pattern 38 becomes high. Further, the closed edge portions 36b, 36b, . . . of the slots 36, 36, . . . which act as the electrophoresis starting edge portions are constituted as substantially sharp cut surfaces and aligned with each other. Therefore, in the operation including the step of comparing multiple migration rows as in the operation of determining the base sequence in DNA or the like, it is possible to improve the accuracy of the information on the base sequence or the like obtained by comparing the migration rows.

Figure 7:
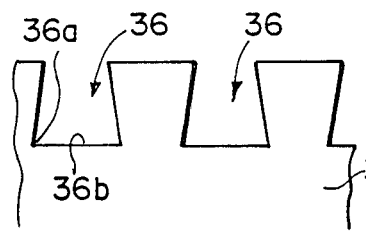
FIGS. 7 and 8 are plan views showing the slot sections of the gel membranes of the electrophoresis sheets made by different embodiments of the method in accordance with the present invention.
Figure 8:
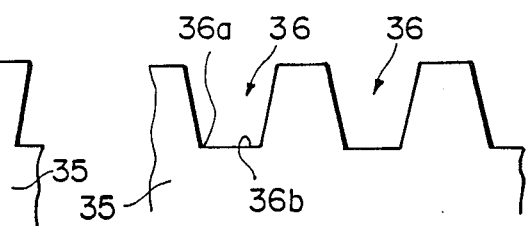
Figure 9:
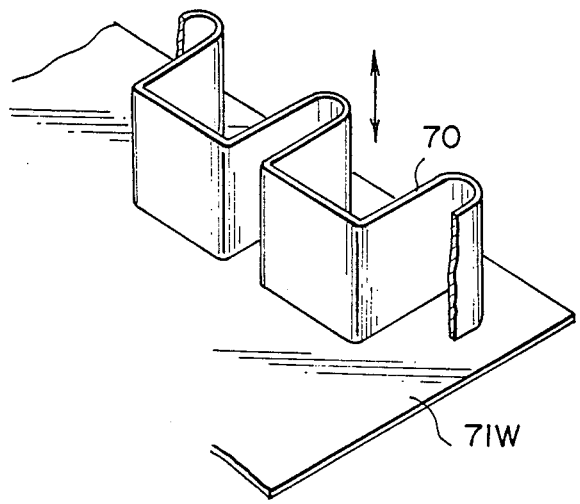
FIG. 9 is a perspective view showing an example of the cutting blade used in the conventional method of making an electrophoresis sheet.
Figure 10:
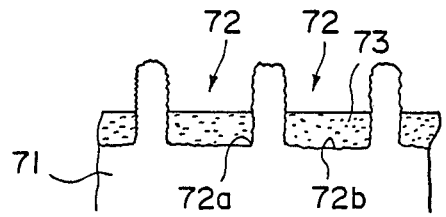
FIG. 10 is a plan view showing the slot section of the gel membrane of the electrophoresis sheet obtained with the conventional method of making an electrophoresis sheet.

In the aforesaid embodiment, the slots 36, 36, . . . of the gel membrane 35 are shaped in the rectangular form, and therefore the slot corners 36a, 36a, . . . are formed at right angles. However, the method of the present invention is applicable also to the case where slots having different shapes are formed. For example, as shown in FIGS. 7 and 8, the slot corners 36a, 36a, . . . can also be formed at acute angles or at obtuse angles by adjusting the angles of the linear longitudinal blades 45, 45, . . . with respect to the linear transverse blade 44 in the cutting blade member 42. Also in this case, it is possible to prevent the slot corners 36a, 36a, . . . from becoming round when the linear longitudinal blades 45, 45, . . . are disposed to continue to the linear transverse blade 44 at both ends of each of the cutaway portions of the single linear transverse blade 44.

I claim:

1. In a method of making an electrophoresis sheet assembly comprising first and second spaced sheet members formed of a non-conductive material, each of said sheets being in an upright position to define a vertical extent and a horizontal extent transverse to said vertical extent, a pair of spacers disposed between said sheets, a separate one of said spacers extending lengthwise adjacent the vertical edges of said sheets, and an electrophoresis gel membrane captured between said first and said second sheet members, said gel membrane, when said sheet assembly is in said upright position, having a plurality of vertically extending and horizontally spaced cut-out slots, wherein the improvement comprises the step of forming said slots by: pushing a cutting blade member against said gel membrane before said gel membrane is grasped between said sheet members, said cutting blade member comprising, in combination:

(a) a single linear front cutting blade disposed to extend in a transverse direction to the longitudinal extent of said gel membrane, said longitudinal extent of said gel membrane corresponding to its vertical extent and said transverse direction corresponding to the horizontal extent of said gel membrane when said sheet assembly is in its upright position, said transverse blade having a plurality of horizontally spaced cutaway portions;

(b) a plurality of linear longitudinal blades disposed to extend in a vertical direction of said gel membrane, the lower portions of the cutting edges of said longitudinal blades contacting edge portions of said transverse blade at the cutting edges defining said cutaway portions;

(c) a plurality of horizontally spaced end blades disposed to extend in a transverse direction of said gel membrane, a separate one of said end blades extending between two adjacent longitudinal blades, the cutting edge portions of said end blade contacting the upper cutting edge portions of said longitudinal blades to locate said end blade in spaced facing relation to a cutaway portion of said transverse blade, said end blades together with said single linear transverse blade and said linear longitudinal blades forming cut-out slots in said gel membrane having sharply cut surface corners; and (d) a linear rear edge cutting blade disposed to extend in a transverse dimension to the longitudinal extent of said gel membrane and in parallel relation to said front transverse blade, said cutting blade member further comprising longitudinally extending side cutting blades extending between said front and rear blades, the lower and upper cutting edge portions of said side blades contacting the respectively adjacent cutting edge portions of said front and rear blades.

2. The method as defined in claim 1, wherein each pair of longitudinal blades that forms a cut-out slot in said gel membrane is perpendicular to said transverse blade.

3. The method as defined in claim 1, wherein each pair of longitudinal blades that forms a cut-out slot in said gel membrane is disposed at acute angles to said transverse blade.

4. The method as defined in claim 1, wherein each pair of longitudinal blades that forms a cut-out slot in said gel membrane is at obtuse angles to said transverse blade.

5. The method of claim 1, wherein said cutting blade member is secured to a rectangular prism-like support block having front, side, rear and top faces, said front cutting blade being secured sto said front face of said block, said side cutting blades being secured to said side faces of said block, and said rear edge cutting blade being secured to said rear face of said block, said block having a plurality of horizontally spaced openings in said top face, each of said openings extending rearwardly and downwardly from the front edge of said top face to also define an opening in said front face of said block, the front edges of said top face which define said openings being aligned with the respective cutaway portions in said front cutting blade, and one of said end blades and an associated pair of longitudinal blades being fitted within each one of said block openings to form, together with said front cutting blade, said cut-out slots.

* * * * *